United States Patent [19]
Johnson et al.

[11] Patent Number: 6,130,321
[45] Date of Patent: *Oct. 10, 2000

[54] HIGH TAP DENSITY CHITOSAN, AND METHODS OF PRODUCTION

[75] Inventors: Edwin Lee Johnson, Issaquah; Everett Junior Nichols, Edmonds, both of Wash.

[73] Assignee: Vanson, Inc., Redmond, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 09/114,023

[22] Filed: Jul. 10, 1998

[51] Int. Cl.$^7$ .................................................. C08B 37/08
[52] U.S. Cl. .................................................. 536/20
[58] Field of Search ................................. 536/20

[56] References Cited

U.S. PATENT DOCUMENTS

| | | | |
|---|---|---|---|
| 4,975,542 | 12/1990 | Hirayama et al. | 536/20 |
| 5,053,113 | 10/1991 | Krepets et al. | 204/130 |

FOREIGN PATENT DOCUMENTS

| | | |
|---|---|---|
| 62-62827 | 3/1987 | Japan . |
| 8-269104 | 10/1996 | Japan . |
| 9-143205 | 6/1997 | Japan . |

OTHER PUBLICATIONS

T. Yui et al., "Molecular and Crystal Structure of the Anhydrous Form of Chitosan", *Macromolecules,* vol. 27, pps. 7601–7605, (Dec. 1994).

G. G. Allan, M. Peyron, "Molecular weight manipulation of chitosan I: kinetics of depolymerization by nitruos acid", *Carbohydrate Research,* vol. 277, pps. 257–272 (1995) month not available.

J. Li, J.F. Revol and R.H. Marchessault, Effect of Degree of Deacetylation of Chitin on the Properties of Chitin Crystallites, John Wiley & Sons, Inc. ccc 0021–8995/97/020373–08., pps. 373–380 (1997) month not available.

Derwent Abstract acc. No. 1987–119188 of JP 62–62827, Mar. 19, 1987, accessed via WEST 1.1 on Dec. 21, 1998.

*Primary Examiner*—Kathleen K. Fonda
*Attorney, Agent, or Firm*—Christensen O'Connor Johnson & Kindness PLLC

[57] ABSTRACT

The present invention provides novel methods of producing chitosan having a tap density of at least about 0.4 g/ml. In one aspect of the present invention, chitosan is selected having an average molecular mass of from about one thousand Daltons to about two million Daltons; a particle size that is smaller than 20 mesh; a viscosity of at least about 1 cps, and a percentage of deacetylation of from about 65% to about 98% A measured amount of the selected chitosan is then mixed with an amount of water that is from about two to about ten times the weight of the chitosan, and an amount of an acid that is at least about 0.1% of the weight of the chitosan. The acid is preferably an organic acid. The mixture of chitosan, water and acid is then mixed to a smooth paste, dried to a moisture content of from 0% moisture to about 20% moisture, and the particle size is preferably reduced to smaller than 20 mesh. In another aspect of the invention, chitosan is provided having a tap density of at least about 0.4 g/ml and the ability to freely flow through an orifice having a circular cross section having a diameter of about 4 mm. The chitosan of the present invention is relatively odorless.

34 Claims, 4 Drawing Sheets

HIGH TAP DENSITY CHITOSAN, AND METHODS OF PRODUCTION

FIELD OF THE INVENTION

This invention relates to chitin and chitosan, and to methods of producing high tap density chitosan.

BACKGROUND OF THE INVENTION

Chitin is a linear polysaccharide composed of β-(1-4)-linked 2-acetamido-2-deoxy-D-glucose units that occurs naturally in the exoskeleton of invertebrates, in particular the carapace of marine crustaceans. Chemical deacetylation of chitin yields chitosan which is a copolymer of 2-amino-2-deoxy-D-glucose and 2-acetamido-2-deoxy-D-glucose units. Chitosan has numerous uses including: an absorbent useful in water purification; a paper wet web strength enhancer; a blood cholesterol lowering compound; a compound useful in adjusting viscosity; a cosmetics additive; a pharmaceutical adjuvant and a dietary supplement.

With respect to the use of chitosan as a water-purifying agent, chitosan is known to bind numerous pollutants of aqueous systems, such as lakes and streams. For example, chitosan has the ability to bind heavy metals and certain halogenated, organic xenobiotics, such as PCPs (pentachlorophenols) and PCBs (polychlorinated biphenyls). Additionally, chitosan complexed with molybdenum is capable of binding orthophosphate ions which pollute lakes and streams. A chitosan preparation having a high density is especially desirable because it will more rapidly sink to the bottom of the body of water to which it is added, thereby sequestering bound contaminants, such as heavy metals, from the bulk of the water. The bound contaminants may therefore be more easily removed from the contaminated, aqueous system.

With respect to the use of chitosan as a dietary supplement, chitosan is often used to reduce the blood serum level of cholesterol, and to promote weight loss by impeding dietary fat absorption in the gastrointestinal tract. Chitosan can be encapsulated or tabletized either alone or in combination with other ingredients including vitamins C, E, B6, β-carotene, folic acid, and a variety of binders. For the benefit of those individuals who have difficulty swallowing tablets or capsules, chitosan can be added to baked goods, such as crackers, cookies and cakes, and to beverages. Again, a high density preparation of chitosan is desirable because, for example, a smaller volume of high density chitosan need be consumed, compared to standard, lower density chitosan, in order to deliver the same dose of chitosan. Thus, for example, a person need consume fewer tablets or capsules of high density chitosan compared to standard preparations of lower density chitosan.

Chitosan is typically utilized in the form of a powder. A problem associated with powdered chitosan, however, is that it has poor flow characteristics as measured by its ability to pass through a narrow orifice without "bridging", i.e., without binding to form a plug within the orifice, thereby stopping flow. These poor flow characteristics make it difficult to handle and dispense large quantities of powdered chitosan. Also, these poor flow characteristics make it difficult to accurately and reproducibly dispense a standard amount of chitosan into, for example, a capsule.

There is therefore a need for a chitosan preparation having improved flow characteristics. Typically, chitosan preparations having increased density also have improved flow characteristics. An art recognized means for increasing the density, and thereby improving the flow characteristics, of powdered chitosan is to "slug" the chitosan powder by wetting the chitosan with water, roller pressing the wet chitosan, drying and regrinding. This process increases the bulk density of the chitosan, i.e., the weight of a chitosan sample divided by its non-packed volume. "Slugging" does not, however, substantially increase the tap density of the chitosan, i.e., the weight of a chitosan sample divided by its packed volume. In other words, "slugging" does not permit substantially more chitosan to be packed into a container, such as a capsule, of constant volume.

Consequently, there is a need for chitosan having high tap density and favorable flow characteristics, and for a process for making the same. Further, there is a need for a high tap density chitosan that has a reduced fish odor compared to the fish odor of existing, low tap density chitosans. A high tap density chitosan having a reduced fish odor is especially desirable for use as a dietary supplement.

SUMMARY OF THE INVENTION

The present invention provides novel methods of producing chitosan having high bulk density and high tap density. In particular, the present invention provides novel methods of producing chitosan having a tap density of at least about 0.4 g/ml. In the methods of the present invention, chitosan is selected having an average molecular mass of between about one thousand and two million Daltons; a particle size that is smaller than about 20 mesh, and a percentage of deacetylation of from about 65% to about 98%, preferably from about 75% to about 90%. A measured amount of the selected chitosan is then mixed with an amount oif water that is from about two to about ten times the weight of the air dried, selected chitosan, preferably about five times the weight of the air dried chitosan, and an amount of an acid that is at least about 0.1% of the weight of the chitosan. Preferably the acid is an organic acid, most preferably succinic acid, malic acid or adipic acid. The mixture of chitosan, water and acid is then mixed to a smooth paste and dried, preferably to a moisture content of from 0% moisture to about 20% moisture. In a particular embodiment, the particle size is reduced, preferably by grinding, to a mesh size smaller than about 20 mesh, preferably smaller than about 40 mesh. The treated chitosan preparation is then preferably sieved to provide chitosan having a uniform particle size and a tap density of at least about 0.4 g/ml. The foregoing methods may also utilize starting chitosan that has a Brookfield Rotational Viscosity of at least about 1 cps. The foregoing methods may also include an optional neutralization step in which the chitosan/water/acid paste is contacted with an amount of a chemical base sufficient to adjust the pH of the paste to about pH 7.0. Alternatively, the neutralization step can be applied after the treated chitosan is dried.

In another aspect of the invention, chitosan is provided having a tap density of at least about 0.4 g/ml and the ability to flow relatively freely through an orifice having a circular cross section with a diameter of about 4 mm, compared to chitosan that was not prepared in accordance with the methods of the present invention. The novel chitosan of the present invention is relatively odorless compared to chitosan that has not been prepared in accordance with the present invention. Chitosan particles of the present invention have a smoother surface than particles of chitosan that have not been prepared in accordance with the present invention.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
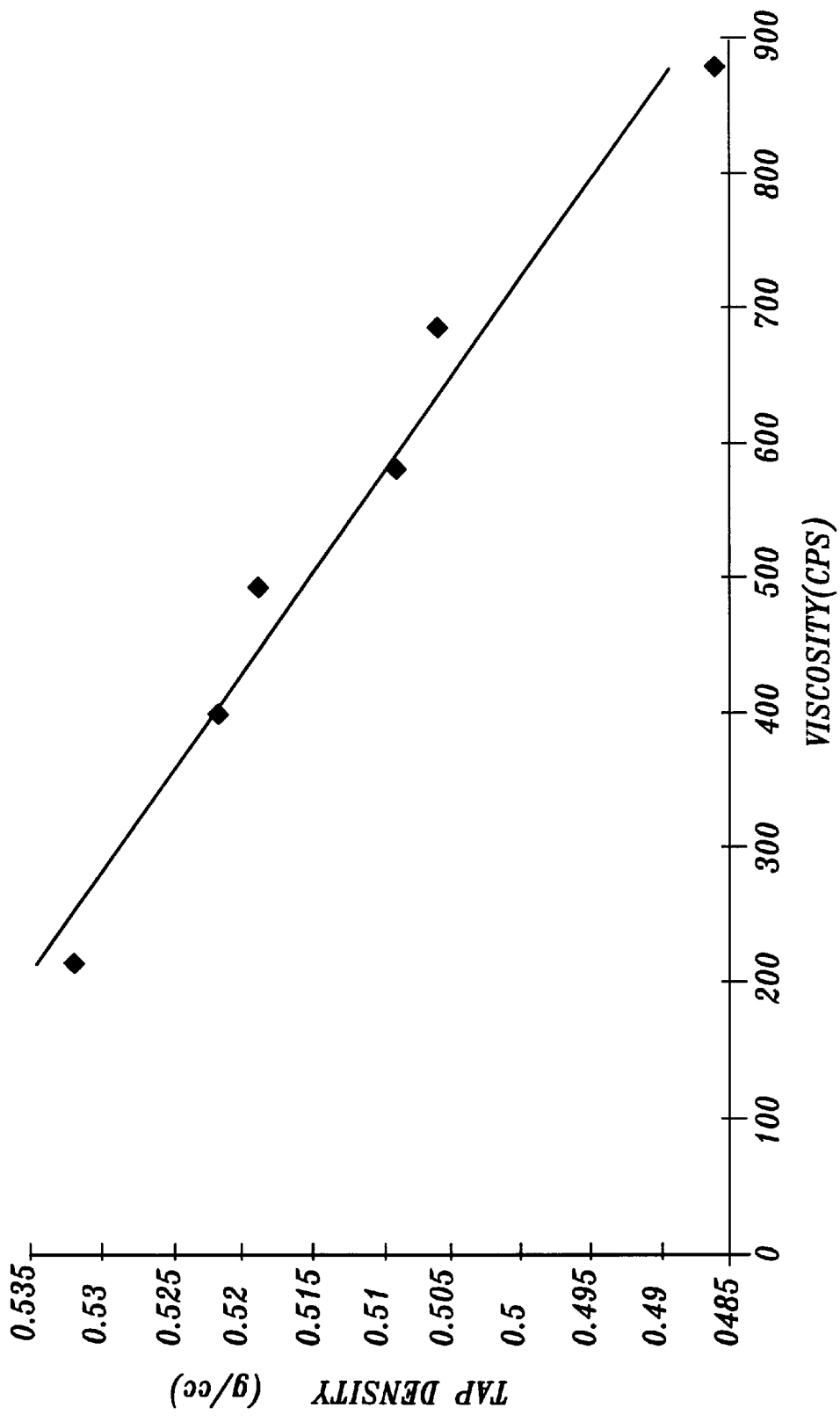
FIG. 1 shows the effect of the viscosity of the chitosan starting material on the tap density of chitosan prepared in accordance with the present invention.

As used herein the term "mesh" refers to the size of a particle as determined by its ability to pass through a screen having holes of defined dimensions. The mesh sizes used herein are Tyler equivalents, as set forth in Table 21-12 of the Chemical Engineers' Handbook, Fifth Edition, R. H. Perry and C. H. Chilton, editors. A plus sign before the mesh number indicates that the particles are larger than that mesh size and do not pass through a screen having the indicated mesh size. A minus sign before the mesh number indicates that the particles are smaller than that mesh size and pass through a screen having the indicated, negative mesh size.

The term "chitin" refers to a linear copolymer of N-acetylglucosamine residues and glucosamnine residues, wherein greater than 98% of the residues that constitute chitin are N-acetylglucosamine residues.

The term "chitosan" refers to a copolymer of glucosamine residues and N-acetylglucosamine residues having a degree of deacetylation of at least 2%, i.e., at least 2% of the residues that constitute chitosan are glucosamine.

The term "bulk density" refers to the weight of a chitosan sample divided by its non-packed volume. The units of bulk density are grams (g) per cubic centimeter (cc), abbreviated as g/cc, or, alternatively, grams (g) per milliliter (ml), abbreviated as g/ml. In the practice of the present invention, the bulk density of chitosan is typically measured by pouring ground chitosan into a 10 ml graduated cylinder and dividing the weight of the chitosan in the cylinder by its volume.

The term "tap density" refers to the weight of a chitosan sample divided by its packed volume. The tap density is determined by placing a chitosan sample into a 10 ml graduated cylinder and recording the weight of the chitosan. The graduated cylinder is then forcefully tapped up and down 300 times on a solid surface until a constant volume is attained, i.e., the volume of the chitosan in the cylinder cannot be reduced further by continued tapping. The weight of the chitosan is divided by its final, constant volume to yield the tap density. The units of tap density are grams (g) per cubic centimeter (cc), abbreviated as g/cc, or, alternatively, grams (g) per milliliter (ml), abbreviated as g/ml.

The present invention provides a novel form of chitosan having a tap density of at least about 0.4 g/ml, and methods for making the same. The methods of the present invention utilizes chitosan that is readily available and is derived from chitin obtained from the exoskeleton of invertebrates, especially marine crustaceans. For example, chitosan useful as a starting material in the practice of the methods of the present invention can be obtained in the following manner. Chitin is first extracted from crustacean shells by soaking the shells in 2M hydrochloric acid at 20° C. to 30° C. for approximately five hours. The demineralized shells are washed with water and then deproteinized by soaking in 1–3% sodium hydroxide at 40° C. to 50° C. for approximately six hours, followed by washing in water. The resulting chitin is then deacetylated by treating with a 50% sodium hydroxide solution at approximately 40° C. to 50° C. for eighteen hours, then washing with water until the pH is approximately 7.0. The resulting chitosan can be ground to a desired mesh size.

The molecular mass of the chitosan useful as starting material in the methods of the present invention should preferably be in the range of from about 1000 Daltons to about 2,000,000 Daltons, most preferably from about 10,000 Daltons to about 1,000,000 Daltons.

It has been found that the particle size of the chitosan used as starting material affects the tap density of the chitosan produced by the process of the present invention. In general, the smaller the particle size of the chitosan used as starting material, the higher will be the tap density of the chitosan produced by the process of the present invention. Preferably, the particle size of the chitosan that is utilized as the starting material in the process of the present invention is smaller than about 20 mesh, most preferably smaller than about 40 mesh. Chitosan powder can be ground to the desired particle size by any art-recognized means, such as the use of a high speed, turbine-type Jacobson grinder.

It has also been found that the viscosity of the chitosan used as starting material affects the tap density of the chitosan produced by the process of the present invention. In general, the lower the viscosity of the chitosan starting material, the higher will be the tap density of the chitosan produced by the process of the present invention. Preferably, the chitosan used as starting material in the process of the present invention should have a viscosity of at least about 1 cps, where the abbreviation "cps" refers to the centipoise unit of viscosity. Typically, viscosity is determined using a 1% (w/w) chitosan solution in the following manner. The chitosan is dissolved in 1% (w/w) glacial acetic acid diluted in distilled water. The chitosan solution is prepared for viscosity determination by adding 1 gram of dry chitosan to 98 grams of distilled water followed by 1 gram of glacial acetic acid and stirred for 2 hours at 25° C. Viscosity is determined at the end of the two hour stirring period at 25° C. using a Brookfield Viscometer.

Additionally, it has been found that the degree of deacetylation of the chitosan starting material affects the tap density of the chitosan produced by the process of the present invention. In general, a high degree of deacetylation of the chitosan starting material results in a reduction in the tap density of the chitosan produced by the process of the present invention. Preferably, the chitosan used as starting material in the process of the present invention will have a percent deacetylation of from about 65% to about 95%, preferably a percent deacetylation of from about 75% to about 90%. Chitin can be deacetylated to produce chitosan useful as a starting material in the practice of the present invention by any art-recognized means, such as by treating chitin with a solution of 50% sodium hydroxide at a temperature of 40° C., or higher. The process of deacetylation occurs more quickly and efficiently at higher temperature.

In the process of the present invention, the chitosan having the foregoing characteristics is mixed with water containing at least one acid. The amount of water added to the chitosan starting material affects the tap density of the chitosan produced by the process of the present invention. The amount of water added to the starting chitosan should be adjusted to allow for the water already present in the starting chitosan, which should preferably be dried to a moisture content of from 0% water to about 20% water. The weight of water added to the starting chitosan should not exceed about ten times the weight of the starting chitosan. Preferably the weight of water added to the starting chitosan is about five times the weight of the starting chitosan. If starting chitosan is mixed with an amount of acid that weighs less than the starting chitosan, and an amount of water that is equal to 10 times or more of the weight of the starting chitosan, then high tap density will not be obtained. Conversely, if starting chitosan is mixed with an amount of acid that weighs more than the starting chitosan, and an amount of water that is 10 times or more the weight of the starting chitosan, then the chitosan will dissolve and form a viscous solution and not remain particulate.

Similarly, the amount of acid added to the chitosan starting material affects the tap density of the chitosan produced by the present process. The weight of acid added to the starting chitosan should be at least about 0.1% of the weight of the starting chitosan that has been dried to a moisture content of from 0% to about 20%. The amount of acid added to the starting chitosan can be adjusted in proportion to the amount of water remaining in the starting chitosan. If an amount of acid is used that approaches, equals or exceeds the weight of the starting chitosan, then the amount of water added to the starting chitosan should be reduced to prevent the chitosan from completely dissolving.

Numerous acids are useful in the practice of the process of the present invention, including, but not limited to: succinic; adipic; hydrochloric; glutamic; lactic; aspartic; acetic; pyruvic and malic. The most effective acids are organic acids that contain at least one carboxyl group. The presently preferred acids are succinic acid; pyruvic acid; malic acid; L-glutamic acid and ascorbic acid.

The starting chitosan is mixed with water and at least one acid for a period of at least one minute, or until the chitosan, water and acid form a homogeneous paste. The treated chitosan is then dried to a moisture content of from 0% to about 20%. Drying can be by any art-recognized means, such as air drying, vacuum drying, heat drying or freeze drying.

An additional, optional step is to neutralize the acid in the chitosan/water/acid paste by adding the paste, before it is dried, to a neutralization bath containing water and a base such as, for example, sodium hydroxide, potassium hydroxide or ammonium hydroxide. The amount of base present is preferably in about ten-fold molar excess of the amount of acid present in the paste. The total volume of the neutralization solution should be sufficient to ensure that the chitosan paste remains sufficiently fluid to permit thorough mixing with the base. Preferably the volume of the neutralization solution is about 10 times the volume of the chitosan paste. The mixture of chitosan, water, acid and base is stirred, the duration of the stirring period is principally determined by the temperature of the mixture. In general, the higher the temperature, the shorter the duration of the stirring period. Thus, for example, at an ambient temperature of from about 20° C. to about 30° C., stirring should continue for at least 18 hours.

The neutralized paste is then preferably rinsed extensively with water in order to remove or wash out the salt of the acid (e.g., sodium succinate where the acid utilized is succinic acid, and the neutralizing base is sodium hydroxide). Alternatively, the neutralization step can be performed after the paste is dried. The dried paste is added to a neutralization bath as described above and stirred for at least 18 hours at ambient temperature, or for a shorter time period at higher temperature. If a base neutralization step is included in the process, a higher concentration of acid can be used to treat the chitosan.

The particle size of the treated chitosan may be reduced in size, preferably by grinding, until a desired particle size is achieved. Thus, for example, a particle size of smaller than 20 mesh, preferably smaller than 40 mesh, is presently preferred for high tap density chitosan of the present invention that is to be used as a dietary supplement. A particle size of greater than 20 mesh is presently preferred for high tap density chitosan of the present invention that is to be used as a water treatment additive for removing, for example, heavy metals from polluted lakes or streams.

The treated, ground chitosan is preferably then sieved by passing it through stacked sieves, with the mesh size decreasing from the top of the stack to the bottom of the stack, i.e., the size of the apertures in the mesh decreases from the top of the stack to the bottom of the stack. The stacked sieves are constantly vibrated so that the chitosan particles pass through the sieves until each particle encounters a sieve which has a mesh size that is too small to permit the particle to pass through. Alternatively, when it is desirable to obtain only chitosan that has a particle size that is smaller than a specified mesh size, then all the chitosan that passes through a single screen having the specified mesh size is collected.

The chitosan produced by the process of the present invention has a tap density of at least about 0.4 g/ml, and preferably at least about 0.5 g/ml. Additionally, the chitosan produced by the process of the present invention has improved flow characteristics. For example, the chitosan produced by the process of the present invention has the ability to freely flow through an orifice having a circular cross section, of diameter of about 4 mm, without "bridging". Further, the chitosan of the present invention has less odor compared to low tap density chitosan preparations.

The novel chitosan of the present invention has numerous uses, including, but not limited to, a dietary supplement useful for lowering the level of cholesterol in the blood, and a bioremediation agent that can be added to an aqueous system, such as a lake, to absorb pollutants such as heavy metals.

The practice of the present invention will be better understood by reference to the following specific examples.

EXAMPLE 1

Increase in Tap Density of Chitosan Following Treatment by a Method of the Present Invention Four samples of starting chitosan were treated in accordance with the methods of the present invention and the resulting tap density of the chitosan samples was determined.

The four chitosan samples were treated under identical conditions. The viscosity of each of the four samples of starting chitosan was determined by using 1% chitosan (w/w) solutions in 1% (w/w) acetic acid. Each sample was prepared by adding 1.00 gram of chitosan to 98.00 grams of distilled water followed by 1.00 gram of glacial acetic acid and stirred with a magnetic stir bar on a stir plate for a minimum of 2 hours. Viscosity was measured using a Brookfield viscometer.

Starting chitosan samples were all −120 mesh material. 10.00 grams of dry −120 mesh chitosan was placed in a beaker. 50.00 grams of distilled water (at an ambient temperature of 20° C. to 30° C.), containing 0.57 grams of dissolved succinic acid, was added to the chitosan and the mixture was stirred and mixed with a spatula for approximately 1 to 5 minutes. The resulting pasty/spongy material was spread out on a stainless steel tray to dry at 60° C. for 18 hours in a convection oven.

Following drying, the material was ground in a laboratory grinding mill (Thomas-Wiley) and particles were reduced in size by shearing action. The ground material was screened through an 80 mesh sieve using a laboratory Thomas Sieve Shaker. The material passing through the 80 mesh sieve (Tyler equivalent) was collected and the tap density was determined by placing a chitosan sample into a 10 ml graduated cylinder and recording the weight of the chitosan. The graduated cylinder was then forcefully tapped up and down 300 times on a solid surface until a constant volume is attained, i.e., the volume of the chitosan in the cylinder could not be reduced further by continued tapping. The weight of the chitosan was divided by the final, constant volume to yield the tap density. Aliquots of the untreated chitosan samples were ground and sieved through the same 80 mesh sieve and the tap densities were determined as set forth above on −80 mesh material. The data set forth in Table 1 shows the effect on tap density of treating the four, starting chitosan samples in accordance with the foregoing method.

TABLE 1

Increase in Bulk Density Following Treatment

| Starting Chitosan Lot (Sample) No. | Viscosity of Starting Chitosan (cps) | Percent Deacetylation of Starting Chitosan | Tap Density (g/ml) Untreated Chitosan | Tap Density (g/ml) Treated Chitosan | Percent Increase in Tap Density |
|---|---|---|---|---|---|
| 014 | 685 | 77% | 0.294 | 0.506 | 72% |
| 504 | 580 | 75% | 0.316 | 0.489 | 55% |
| 012 | 470 | 73% | 0.352 | 0.538 | 53% |
| 917 | 495 | 75% | 0.316 | 0.519 | 64% |

The results set forth in Table 1 demonstrate that the tap density of the four samples of chitosan starting material was increased by more than fifty percent by treatment of the starting chitosan in accordance with the process of the present invention.

EXAMPLE 2

Comparison of Flow Properties of Untreated Chitosan and Chitosan Treated According to the Process of the Present Invention The ability of chitosan treated in accordance with the process of the present invention to flow through a narrow orifice was evaluated in the following manner.

All of the chitosan came from the same batch and lot. The viscosity of the starting material chitosan was 470 cps. The percent deacetylation of the starting chitosan was 73% and the pretreatment tap density of the −80 mesh starting chitosan material was 0.352 grams/cc. High density chitosan was prepared in accordance with the methods of the present invention as described in Example 1.

After grinding, the treated, high density chitosan was sieved over a series of sieves of 50 mesh, 60 mesh, 80 mesh, 100 mesh and 120 mesh sizes. Material was collected on all screens and the tap densities were determined for each mesh size collected. For example, material that passed through a 50 mesh sieve and was retained on a 60 mesh sieve was collected and the tap density determined. This material is denoted as −50+60 chitosan. The tap densities of all treated chitosan samples exceeded 0.45 g/ml. The starting chitosan (untreated) was sieved and collected in the same way and the tap densities determined for the various mesh sizes.

Flow measurements were performed in the following manner. 5.00 grams of treated or non-treated chitosan screened to the indicated mesh size was added to a circular glass funnel sloping at an angle of 60° with respect to the stem. The funnel stem measured 38 mm in length having a 4 mm diameter circular orifice. The funnel was mounted in a perpendicular position to the horizontal plane of the lab bench. The time for the chitosan to completely leave the funnel with or without tapping of the funnel was recorded.

Flowability experiments were repeated in triplicate with the −120 mesh and −50+60 mesh treated and untreated chitosan. Values shown are mean values from three determinations. The results are shown below in Table 2.

TABLE 2

Flowability of Treated and Untreated Chitosan

| Mesh Size | Sample | Funnel Flow Time |
|---|---|---|
| −50 + 60 | Treated High Density Chitosan | 4 seconds |
| −50 + 60 | Non-Treated Chitosan | fluff, no flow |
| −120 mesh | Treated High Density Chitosan | 7 seconds w/tapping |
| −120 mesh | Non-Treated Chitosan | 163 seconds w/tapping |

The data set forth in Table 2 demonstrates that chitosan treated in accordance with the process of the present invention has improved flow characteristics compared to chitosan that is not treated in accordance with the process of the present invention.

EXAMPLE 3

The Effect of the Viscosity of the Starting Chitosan on the Tap Density of Chitosan Produced in Accordance with the Process of the Present Invention The effect of the viscosity of the chitosan starting material on the tap density of the chitosan produced in accordance with the process of the present invention was evaluated in the following manner. Starting chitosan samples were all −120 mesh. The viscosity of the starting chitosan was determined using a Brookfield Viscometer. The treatment conditions were as described in Example 1. In brief, 10 grams of −120 mesh chitosan were mixed to a pasty/spongy consistency with 50 grams of water containing 0.57 grams of dissolved succinic acid. The mixture was dried at 60° C., then ground and sieved to yield particles of −80 mesh. Tap densities were determined on −80 mesh material as described in Example 1. The results are shown in FIG. 1.

The results shown in FIG. 1 demonstrate that, in general, the lower the viscosity of the chitosan starting material utilized in the process of the present invention, the higher will be the tap density of the treated chitosan.

EXAMPLE 4

Figure 2:
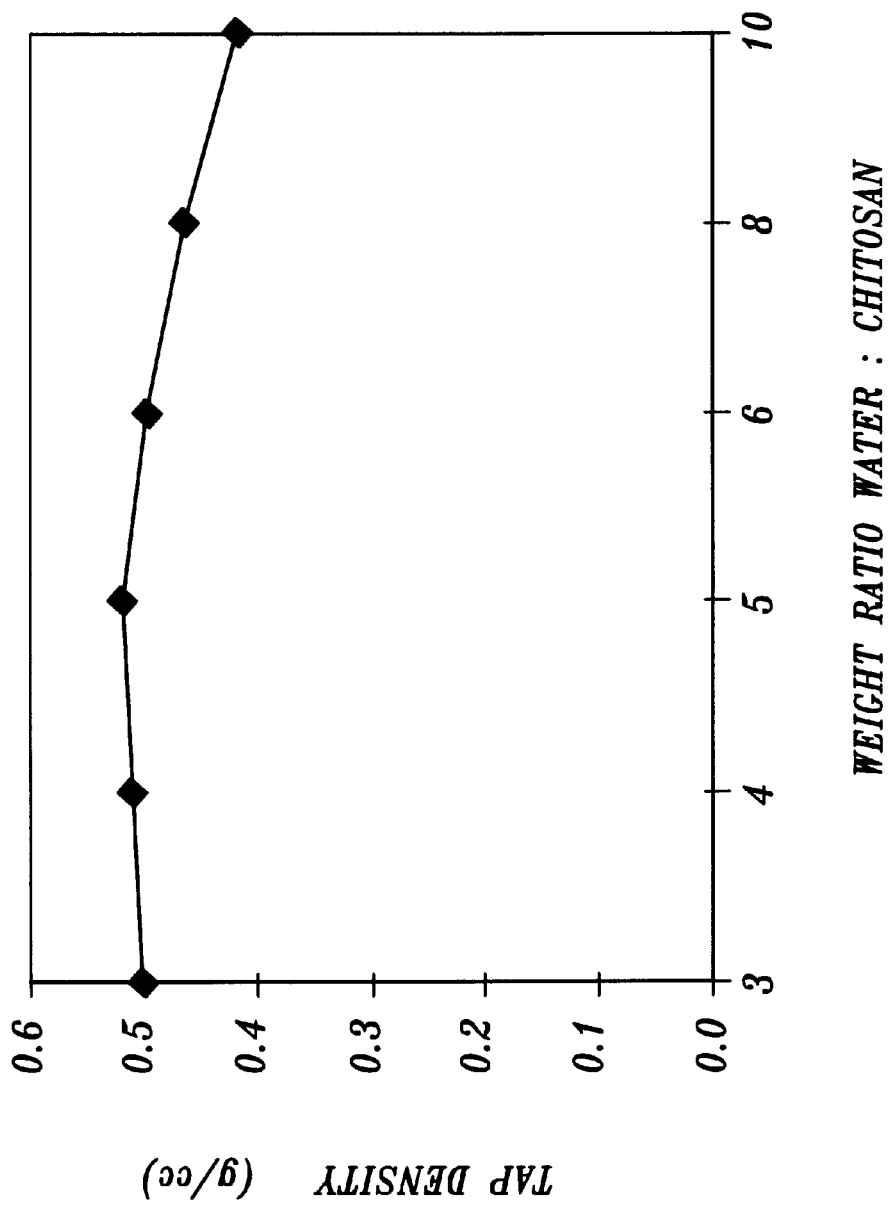
FIG. 2 shows the effect of the ratio of water to chitosan starting material on the tap density of chitosan prepared in accordance with the present invention.

The Effect of the Ratio of Water to Starting Chitosan on the Tap Density of the Chitosan Produced in Accordance with the Process of the Present Invention The effect of the ratio of water to starting chitosan on the tap density of chitosan produced according to the process of the present invention was determined in the following manner. 10 gram aliquots of −120 mesh chitosan, all taken from the same lot, were treated with succinic acid in an amount equal to 5.7% of the weight of the chitosan. The succinic acid was dissolved in amounts of water equal to 3 times, 4 times, 5 times, 6 times, 8 times or 10 times the weight of the dry chitosan used. For example, 10 grams chitosan were added to 0.57 grams of succinic acid dissolved in 30 grams, or 40 grams, or 50 grams or 60 grams or 80 grams or 100 grams of water. The mixture was mixed to a pasty/spongy consistency, dried at 60° C., ground, sieved through a −80 mesh sieve and tap densities were determined on −80 mesh material. The results of these experiments are set forth in FIG. 2.

EXAMPLE 5

The Effect of Various Acids on Chitosan Tap Density

The ability of a variety of acids to increase chitosan tap density when utilized in the process of the present invention was investigated in the following manner. Since the different acids used in this study differ in molecular weight, the amount of each acid utilized was the molar equivalent of an amount of succinic acid that is 5.7% of the weight of the chitosan starting material. If the foregoing molar equivalent amount of acid used was not completely soluble at ambient temperature (20° C. to 30° C.), then the solution was heated to at least 45° C. to dissolve the acid. The heated solution containing the dissolved acid was then added to the chitosan and the mixture stirred. The chitosan starting material was treated as described in Example 1.

When other acids are used at an equivalent molar concentration to that of succinic acid (used at 5.7% weight of the starting chitosan), these acids are effective at increasing tap density to greater than 0.40 g/cc. The results are shown in Table 3 below.

TABLE 3

Chitosan Tap Density Comparisons Using Various Acids at Molar Concentrations Equivalent to an Amount of Succinic Acid that is 5.7% the Weight of the Chitosan Starting Material

| Starting Chitosan Mesh Size | Acid Type | Molar Equiv. to % Succinic Acid | Treated Chitosan Tap Density (grams/cc) | Treated Chitosan Mesh Size |
|---|---|---|---|---|
| −120 | Control, no acid | NA | 0.35 | −80 |
| −120 | succinic | 5.7% | 0.58 | −80 |
| −120 | fumaric | 5.7% | 0.52* | −80 |
| −120 | L-glutamic | 5.7% | 0.54* | −80 |
| −120 | hydrochloric | 5.7% | 0.46 | −80 |
| −120 | glucuronic | 5.7% | 0.49 | −80 |
| −120 | citric | 5.7% | 0.42 | −80 |
| −120 | lactic | 5.7% | 0.43 | −80 |
| −120 | malonic | 5.7% | 0.41 | −80 |
| −120 | ascorbic | 5.7% | 0.50 | −80 |
| −120 | aspartic | 5.7% | 0.49* | −80 |
| −120 | acetic | 5.7% | 0.51 | −80 |
| −120 | malic | 5.7% | 0.49 | −80 |
| −120 | pyruvic | 5.7% | 0.52 | −80 |
| −120 | maleic | 5.7% | 0.44 | −80 |

*Solution was heated to dissolve acid.

The data set forth in Table 3 reveal that the acids which are effective in the process of the present invention include, but are not limited to: succinic, fumaric, hydrochloric, glucuronic, citric, lactic, malonic, ascorbic, aspartic, acetic, malic, pyruvic and maleic.

The acids were also examined at molar equivalent concentrations to an amount of succinic acid that is equal to 28% of the weight of the starting chitosan. If the maximum ambient temperature solubility of the acid was lower than the amount of acid required to provide a molar equivalent to succinic acid (used at 28% of the weight of chitosan), then the concentration was defined as a saturated solution of the acid at ambient temperature (20° C. to 30° C.). Heat was not applied to dissolve the acid. The chitosan starting material was treated as described in Example 1, except that the mesh size of the treated chitosan was as set forth in Table 4. Results are set forth in Table 4.

TABLE 4

Chitosan Tap Density Comparisons Using Various Acids at Molar Concentrations Equivalent to an Amount of Succinic Acid that is 28% the Weight of the Chitosan Starting Material

| Starting Chitosan Mesh Size | Acid Type | Molar Equiv. to 28% Succinic Acid | Treated Chitosan Tap Density (grams/cc) | Final Chitosan Mesh Size |
|---|---|---|---|---|
| −120 | control, no acid | 0 | not determined | −50 + 80 |
| −120 | control, no acid | 0 | 0.28 | −80 + 120 |
| −120 | control, no acid | 0 | 0.30 | −120 |
| −120 | succinic | 28 | 0.71 | −50 + 80 |
| −120 | succinic | 28 | 0.65 | −80 + 120 |
| −120 | succinic | 28 | 0.59 | −120 |
| −120 | fumaric | saturated sol. | 0.52 | −50 + 80 |
| −120 | fumaric | saturated sol. | 0.42 | −80 + 120 |
| −120 | fumaric | saturated sol. | 0.52 | −120 |
| −120 | glutamic | saturated sol. | 0.29 | −50 + 80 |
| −120 | glutamic | saturated sol. | 0.34 | −80 + 120 |
| −120 | glutamic | saturated sol. | 0.39 | −120 |
| −120 | hydrochloric | 28 | 0.54 | −50 + 80 |
| −120 | hydrochloric | 28 | not determined | −80 + 120 |
| −120 | hydrochloric | 28 | 0.49 | −120 |
| −120 | glucuronic | 28 | 0.67 | −50 + 80 |
| −120 | glucuronic | 28 | 0.65 | −80 + 120 |
| −120 | glucuronic | 28 | 0.68 | −120 |
| −120 | citric | 28 | 0.79 | −50 + 80 |
| −120 | citric | 28 | 0.77 | −80 + 120 |
| −120 | citric | 28 | 0.78 | −120 |
| −120 | lactic (synthetic) | 28 | 0.55 | −50 + 80 |
| −120 | lactic (synthetic) | 28 | not determined | −80 + 120 |
| −120 | lactic (synthetic) | 28 | 0.56 | −120 |
| −120 | lactic (natural) | 28 | 0.58 | −50 + 80 |
| −120 | lactic (natural) | 28 | not determined | −80 + 120 |
| −120 | lactic (natural) | 28 | 0.57 | −120 |
| −120 | malonic | 28 | 0.66 | −50 + 80 |
| −120 | malonic | 28 | 0.41 | −80 + 120 |
| −120 | malonic | 28 | 0.66 | −120 |
| −120 | ascorbic | 28 | 0.71 | −50 + 80 |
| −120 | ascorbic | 28 | 0.68 | −80 + 120 |
| −120 | ascorbic | 28 | 0.68 | −120 |
| −120 | aspartic | saturated sol. | not determined | −50 + 80 |
| −120 | aspartic | saturated sol. | 0.35 | −80 + 120 |
| −120 | aspartic | saturated sol | 0.39 | −120 |
| −120 | adipic | 28 | 0.55 | −50 + 80 |
| −120 | adipic | 28 | 0.51 | −80 + 120 |
| −120 | adipic | 28 | 0.70 | −120 |
| −120 | acetic | 28 | 0.59 | −50 + 80 |
| −120 | acetic | 28 | not determined | −80 + 120 |
| −120 | acetic | 28 | 0.53 | −120 |
| −120 | malic | 28 | 0.67 | −50 + 80 |
| −120 | malic | 28 | not determined | −80 + 120 |
| −120 | malic | 28 | 0.67 | −120 |
| −120 | pyruvic | 28 | 0.64 | −50 + 80 |
| −120 | pyruvic | 28 | 0.62 | −80 + 120 |
| −120 | pyruvic | 28 | 0.66 | −120 |
| −120 | maleic | 28 | 0.63 | −50 + 80 |
| −120 | maleic | 28 | not determined | −80 + 120 |
| −120 | maleic | 28 | 0.63 | −120 |

When used at saturating concentrations, or the molar equivalent to 28% succinic acid, the majority of the acids tested were effective at increasing the tap density to greater than 0.40 g/ml. The acids not effective were glutamic acid, aspartic and fumaric.

EXAMPLE 6

The Effect of Increased Acid and the Addition of a Neutralization Step on Tap Density As set forth previously herein, when high concentrations of acid are used in the process of the present invention (such as in the preparation of the high tap density chitosan samples set forth in Table 4), the resulting high tap density chitosan should preferably be treated with a base solution to neutralize the acid. The resulting acid salt can then be rinsed away with water while maintaining the high tap density. The effect on tap density of treating starting chitosan with an increased amount of acid and also incorporating a neutralization step was investigated in the following manner.

Tap densities were determined on dry chitosans ground to smaller than 80 mesh. Neutralization was performed by stirring the dry or wet paste in 1% sodium hydroxide in water for 18 hours at ambient temperature (20° C. to 30° C.) followed by rinsing extensively in water to pH 7. The control treatment consisted of mixing chitosan with the same amount of water minus the acid, drying and grinding to smaller than 80 mesh. The amount of water used was 5 times the weight of chitosan used. Otherwise, samples were treated as set forth in Example 1. The results are set forth in Table 5.

TABLE 5

Effect of Increased Acid and Neutralization on Tap Density

| Mesh Size of Starting Chitosan | % Succinic Acid | Neutralization | Tap Density (g/ml) |
| --- | --- | --- | --- |
| −120 | 28 | none | 0.77 |
| −120 | 28 | before drying | 0.65 |
| −120 | 28 | after drying | 0.76 |
| −120 | 0 (control) | none | 0.35 |
| −50 | 28 | before drying | 0.61 |
| −50 | 28 | after drying | 0.76 |

The data set forth in Table 5 demonstrate that the use of relatively high acid concentrations, and the inclusion of a neutralization step, in the methods of the present invention yields high tap density chitosan.

EXAMPLE 7

Bulk Density Values Compared to Tap Density Values for Treated and Untreated Chitosan Bulk density and tap density were determined using a range of mesh sizes of untreated chitosan and chitosan treated in accordance with a method of the present invention. Treated chitosan was treated as set forth in Example 1. The acid used to treat the chitosan samples was succinic acid in an amount equal to 5.7% of the weight of the dry, starting chitosan. Tap density and bulk density were measured in accordance with the methods set forth in the definition of those terms provided herein. The results are set forth in Table 6, below. Chitosan lots K80771012, K50A80210 and K50J80206 are three separate lots of control, untreated chitosan. Chitosan lot SRW-2398 is succinic acid-treated chitosan.

TABLE 6

Table of Density and Compressibility Index Values

| Mesh Size | Chitosan Lot No. | Bulk Density (gm/cc) | Tap Density (gm/cc) | C.I. Value |
| --- | --- | --- | --- | --- |
| +20 | Lot# K80771012 | N/A | N/A | N/A |
|  | Lot# K50A80210 | N/A | N/A | N/A |
|  | Lot# K50J80206 | N/A | N/A | N/A |
|  | Lot# SRW-2398 | 0.47 | 0.51 | 7.8% |
| −20 + 50 | Lot# K80771012 | N/A | N/A | N/A |
|  | Lot# K50A80210 | N/A | N/A | N/A |
|  | Lot# K50J80206 | N/A | N/A | N/A |
|  | Lot# SRW-2398 | 0.46 | 0.52 | 11.5% |
| −50 | Lot# K80771012 | N/A | N/A | N/A |
|  | Lot# K50A80210 | 0.20 | 0.29 | 33.3% |
|  | Lot# K50J80206 | 0.20 | 0.30 | 33.3% |
|  | Lot# SRW-2398 | 0.42 | 0.53 | 21.9% |
| −50 + 80 | Lot# K80771012 | N/A | N/A | N/A |
|  | Lot# K50A80210 | 0.21 | 0.25 | 16.0% |
|  | Lot# K50J80206 | 0.18 | 0.25 | 28.0% |
|  | Lot# SRW-2398 | 0.50 | 0.54 | 7.4% |
| −80 + 120 | Lot# K80771012 | 0.19 | 0.30 | 36.7% |
|  | Lot# K50A80210 | 0.18 | 0.26 | 30.8% |
|  | Lot# K50J80206 | 0.18 | 0.25 | 28.0% |
|  | Lot# SRW-2398 | 0.44 | 0.51 | 13.7% |
| −120 | Lot# K80771012 | 0.19 | 0.32 | 40.6% |
|  | Lot# K50A80210 | 0.18 | 0.29 | 37.9% |
|  | Lot# K50J80206 | 0.18 | 0.32 | 43.8% |
|  | Lot# SRW-2398 | 0.44 | 0.57 | 22.8% |

The C.I. values set forth in Table 6 are Compressibility Index values (also known as Carrs Index values) which are a measure of flowability. The C.I. value is derived by dividing the bulk density by the tap density to yield a fraction which is subtracted from 1, and the resulting value is multiplied by 100. In general, chitosan particles having a Carrs value less than 15 have excellent flow properties; chitosan particles having a Carrs value between 15 and 25 have good flow properties, while chitosan particles having a Carrs value greater than 25 have poor flow properties. The data set forth in Table 6 demonstrate that the chitosan treated in accordance with a method of the present invention has excellent flow properties.

EXAMPLE 8

Figure 3:
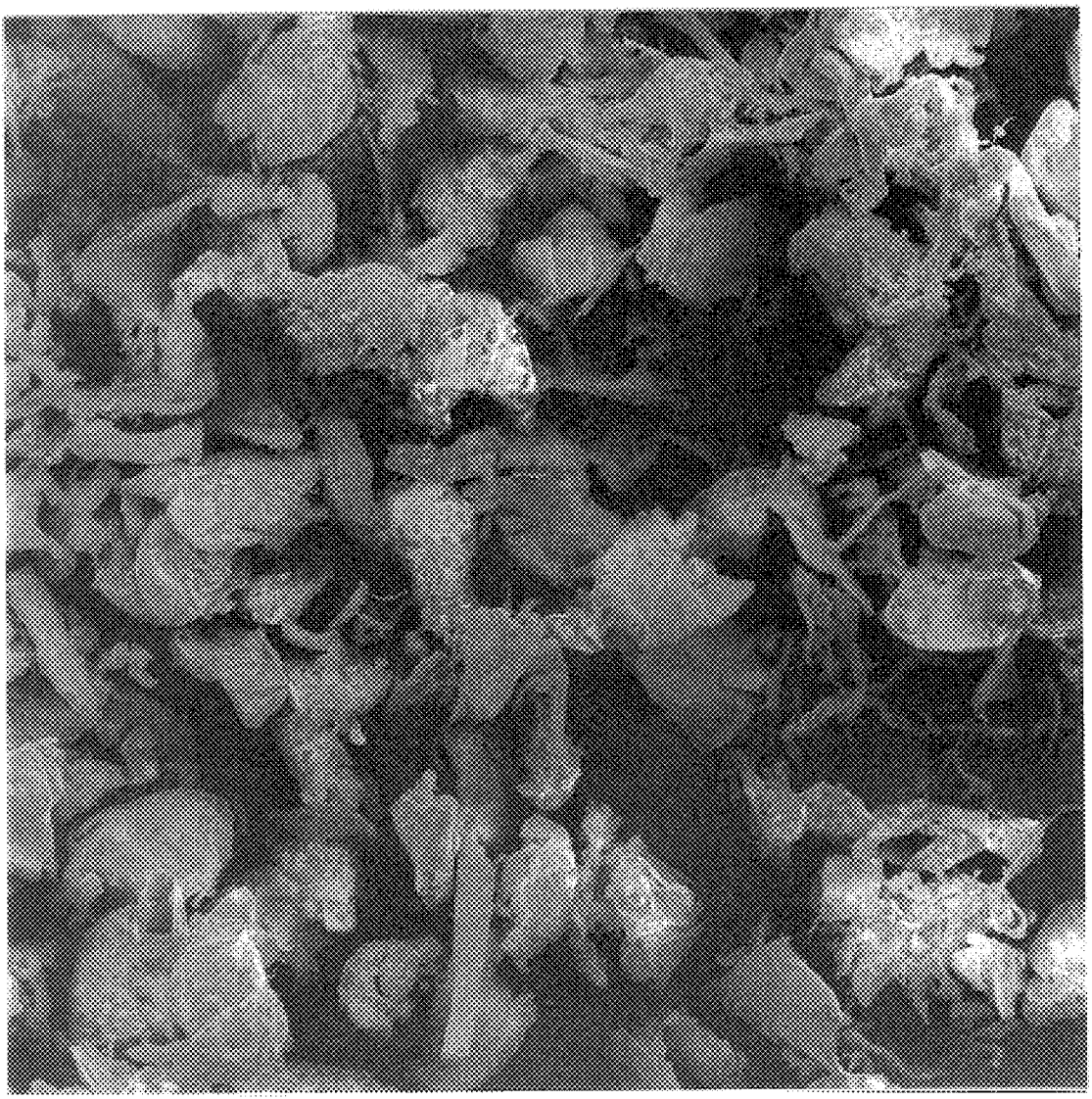
FIG. 3 shows a 50× magnification, scanning electron microscope image of particles of chitosan prior to treatment in accordance with the methods of the present invention.
Figure 4:
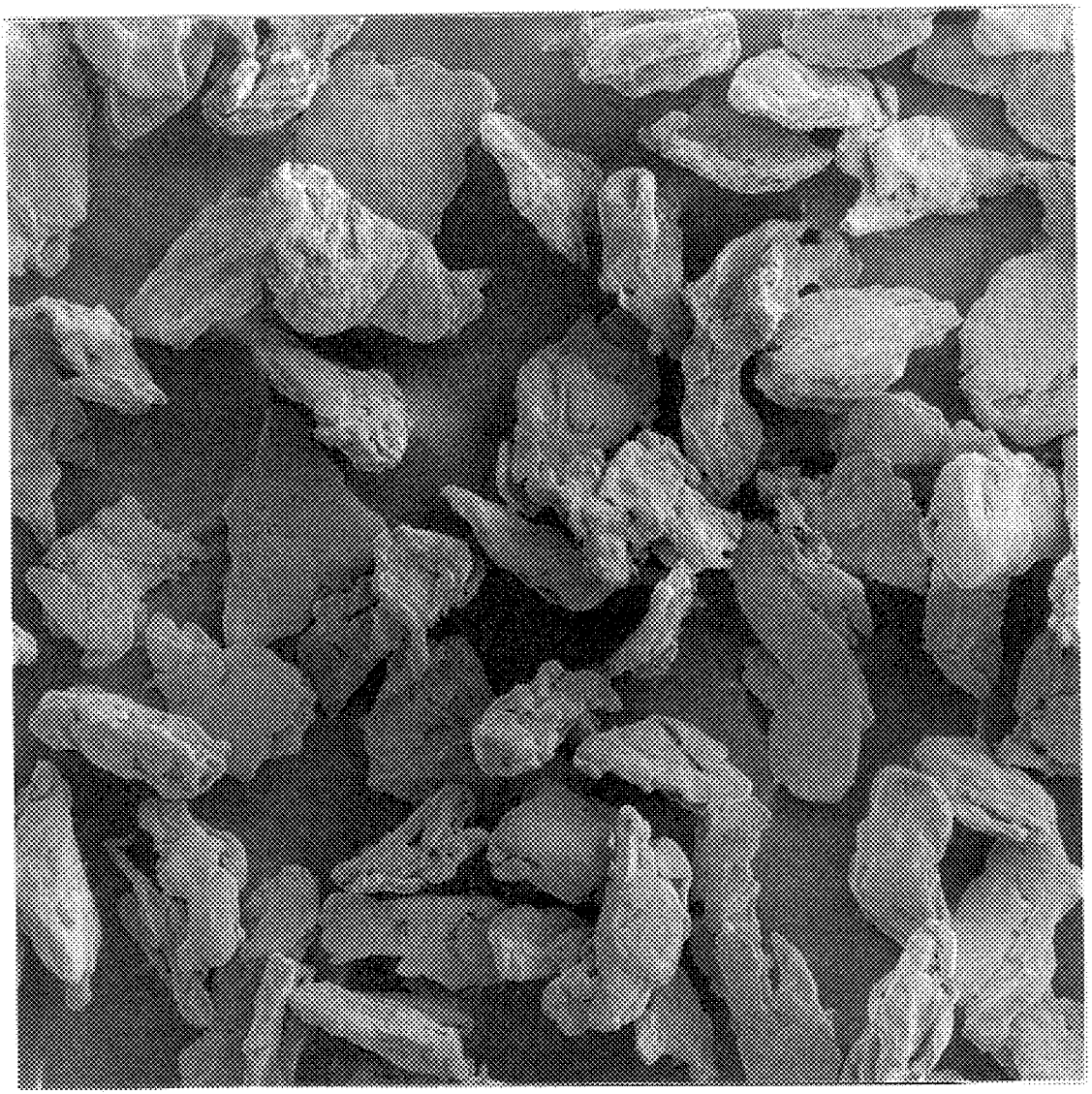
FIG. 4 shows a 50× magnification, scanning electron microscope image of particles of chitosan treated in accordance with the methods of the present invention.

Particle Structure of Chitosan Treated in Accordance with the Methods of the Present Invention Chitosan was treated as set forth in Example 1 and the structure of the treated chitosan particles, and control, untreated chitosan particles, was examined at 50× magnification utilizing a scanning electron microscope. FIG. 3 shows the particle structure of untreated chitosan particles. The particles have an irregular outline and a surface from which fibrous strands project. The untreated chitosan particles also tend to clump together as shown in FIG. 3. In contrast, and as shown in FIG. 4, particles of chitosan treated in accordance with the methods of the present invention have a relatively smooth surface and less variation in particle shape compared to untreated chitosan particles. The fibrous projections extending from the untreated chitosan particles are more readily apparent when the particles are viewed under a binocular optical microscope.

While the present inventors do not wish to be bound to a particular theory of how the methods of the present invention produce chitosan having high tap density, the relative absence of fibrous projections on the surface of particles of chitosan treated in accordance with the methods of the present invention may permit the particles to be more closely packed, thereby increasing tap density relative to untreated chitosan. The fibrous surface of particles of untreated chitosan may entangle the particles and prevent dense packing thereof.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of producing chitosan having a tap density of at least 0.4 g/ml comprising:

mixing chitosan with an effective amount of water and an effective amount of acid; and drying the mixture of chitosan, water and acid.

2. The method of claim 1 wherein the chitosan, prior to mixing with an effective amount of water and an effective amount of acid, has an average molecular mass of from about one thousand Daltons to about two million Daltons.

3. The method of claim 1 wherein the chitosan, prior to mixing with an effective amount of water and an effective amount of acid, has a Brookfield rotational viscosity of from about 1 cps to about 200,000 cps.

4. The method of claim 1 wherein the chitosan, prior to mixing with an effective amount of water and an effective amount of acid, is in the form of particles having a particle size smaller than about 20 mesh.

5. The method of claim 4 wherein the chitosan, prior to mixing with an effective amount of water and an effective amount of acid, is in the form of particles having a particle size smaller than about 50 mesh.

6. The method of claim 1 wherein the chitosan, prior to mixing with an effective amount of water and an effective amount of acid, has a percentage of deacetylation of from about 65% to about 98%.

7. The method of claim 6 wherein the chitosan, prior to mixing with an effective amount of water and an effective amount of acid, has a percentage of deacetylation of from about 75% to about 90%.

8. The method of claim 1 wherein the effective amount of water has a weight that is from about two to about ten times the weight of the chitosan with which the water is mixed.

9. The method of claim 8 wherein the effective amount of water has a weight that is about five times the weight of the chitosan with which the water is mixed.

10. The method of claim 1 wherein the effective amount of acid has a weight that is at least about 0.1 percent of the weight of the chitosan with which the acid is mixed.

11. The method of claim 10 wherein the effective amount of acid has a weight that is from about 2% to about 12% of the weight of the chitosan with which the acid is mixed.

12. The method of claim 1 wherein the acid is an organic acid.

13. The method of claim 1 wherein the acid is selected from the group consisting of succinic acid, adipic acid, hydrochloric acid, glutamic acid, lactic acid, aspartic acid, acetic acid, ascorbic acid, pyruvic acid, malic acid, fumaric acid, citric acid, formic acid, glucuronic acid, sorbic acid, folic acid and maleic acid.

14. The method of claim 1 wherein said mixture of chitosan, water and acid is dried to a moisture content of from 0% moisture to about 20% moisture.

15. The method of claim 1 further comprising the step of reducing the particle size of the dried chitosan to a particle size that is smaller than about 20 mesh.

16. The method of claim 1 further comprising the step of reducing the particle size of the dried chitosan to a particle size that is smaller than about 40 mesh.

17. The method of claim 1 further comprising the step of reducing the particle size of the dried chitosan to a particle size that is smaller than about 120 mesh.

18. The method of claim 1 further comprising a neutralization step.

19. The method of claim 18 wherein the neutralization step comprises contacting the mixture of chitosan, water and an acid with an amount of a base sufficient to neutralize the acid, said mixture being contacted with said base before said mixture is dried.

20. The method of claim 18 wherein the neutralization step comprises contacting the dried mixture of chitosan, water and an acid with an amount of a base sufficient to neutralize the acid.

21. A method of producing chitosan having a tap density of at least about 0.4 g/ml comprising:

mixing chitosan with an effective amount of water and an acid, said chitosan having an average molecular weight of from about one thousand Daltons to about two million Daltons; a particle size that is smaller than about 20 mesh; a viscosity of at least about 1 cps and a percentage of deacetylation of from about 65% to about 98%; and drying the mixture of chitosan, water and acid.

22. A method of producing chitosan having a tap density of at least about 0.4 g/ml comprising:

mixing chitosan with an effective amount of water and an acid, said chitosan having an average molecular weight of from about one thousand Daltons to about two million Daltons; a particle size that is smaller than about 20 mesh; a viscosity of at least about 1 cps and a percentage of deacetylation of from about 65% to about 98%;

said effective amount of water having a weight that is from about two to about ten times the weight of the chitosan with which the water is mixed;

said effective amount of acid having a weight that is from at least about 0.1 percent of the weight of the chitosan with which the acid is mixed; and drying the mixture of chitosan, water and acid.

23. Chitosan produced by the method of claim 1 having a tap density of at least about 0.4 g/ml.

24. Chitosan produced by the method of claim 1 having a tap density of at least about 0.5 g/ml.

25. Chitosan produced by the method of claim 1 having a bulk density of at least about 0.3 g/ml and a tap density of at least about 0.4 g/ml.

26. Chitosan produced by the method of claim 1 having a bulk density and a tap density each of at least about 0.4 g/ml.

27. Chitosan having a tap density of at least about 0.4 g/ml.

28. Chitosan having a tap density of at least about 0.5 g/ml.

29. Chitosan having a bulk density of at least about 0.4 g/ml.

30. Chitosan having a bulk density of at least about 0.5 g/ml.

31. Chitosan having a bulk density of at least about 0.3 g/ml and a tap density of at least about 0.4 g/ml.

32. Chitosan having a bulk density and a tap density each of at least about 0.4 g/ml.

33. Chitosan of claim 23 wherein said chitosan is selected from the group consisting of chitosan succinate, chitosan adipate, chitosan chloride, chitosan glutamate, chitosan lactate, chitosan aspartate, chitosan acetate, chitosan pyruvate, and chitosan malate.

34. Chitosan of claim 27 wherein said chitosan is selected from the group consisting of chitosan succinate, chitosan adipate, chitosan chloride, chitosan glutamate, chitosan lactate, chitosan aspartate, chitosan acetate, chitosan pyruvate, and chitosan malate.

* * * * *